(12) United States Patent
Inose et al.

(10) Patent No.: US 7,521,183 B2
(45) Date of Patent: Apr. 21, 2009

(54) **METHOD FOR DETECTING *CHLAMYDIA TRACHOMATIS* AND KIT THEREFOR**

(75) Inventors: Ken Inose, Kyoto (JP); Miki Horii, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 0 days.

(21) Appl. No.: 10/545,852

(22) PCT Filed: Feb. 27, 2004

(86) PCT No.: PCT/JP2004/002435

§ 371 (c)(1),
(2), (4) Date: Aug. 17, 2005

(87) PCT Pub. No.: WO2004/076694

PCT Pub. Date: Sep. 10, 2004

(65) Prior Publication Data

US 2006/0246447 A1  Nov. 2, 2006

(30) Foreign Application Priority Data

Feb. 27, 2003  (JP)  .............................. 2003-050662

(51) Int. Cl.
*C12Q 1/68* (2006.01)
*C12P 19/34* (2006.01)

(52) U.S. Cl. .......................................... 435/6; 435/91.2

(58) Field of Classification Search .................... None
See application file for complete search history.

(56) References Cited

U.S. PATENT DOCUMENTS 5,232,829 A    8/1993  Longiaru et al.
6,004,826 A   12/1999  Segev

FOREIGN PATENT DOCUMENTS

| EP | 0 336 412 A2 | 10/1989 |
| EP | 0 812 921 A2 | 12/1997 |
| WO | WO 00/34483 A2 | 6/2000 |
| WO | WO 01/73129 | 10/2001 |
| WO | WO 02/52043 | 4/2002 |

OTHER PUBLICATIONS

Hatt et al. Analysis of the entire nucleotide sequence of the cryptic plasmid of *Chlamydia trachomatis* serovar L1. Evidence for involvement in DNA replication. Nucleic Acids Res. (1988) 16:4053-4067.*
Buck et al., Design strategies and performance of custom DNA sequencing primers. BioTechniques (1999) 27:528-536.*
Welch et al. Detection of plasmid DNA from all *Chlamydia trachomatis* serovars with a two-step polymerase chain reaction. Appl. Environ. Microbiology (1990) 56:2494-2498.*
Comanducci, et al. "Diversity of the *Chlamydia trachomatis* Common Plasmid in Biovars with Different Pathogenicity," *Plasmid*, vol. 23, pp. 149-154, 1990.
Mahony, et al. "Comparison of Plasmid- and Chromosome-Based Polymerase Chain Reaction Assays for Detecting *Chlamydia trachomatis* Nucleic Acids," *Journal of Clinical Microbiology*, vol. 31, No. 7, pp. 1753-1758, Jul. 1993.
Morré, et al. "RNA Amplification by Nucleic Acid Sequence-Based Amplification with an Internal Standard Enables Reliable Detection of *Chlamydia trachomatis* in Cervical Scrapings and Urine Samples," *Journal of Clinical Microbiology*, vol. 34, No. 12, pp. 3108-3114, Dec. 1996.
Østergaard, et al. "Use of Polymerase Chain Reaction for Detection of *Chlamydia trachomatis,*" *Journal of Clinical Microbiology*, vol. 28, No. 6, pp. 1254-1260, Jun. 1990.
Roosendaal, et al. "Comparison of Different Primer Sets for Detection of *Chlamydia trachomatis* by the Polymerase Chain Reaction," *Journal of Medical Microbiology*, vol. 38, pp. 426-433, 1993.
Valassina, et al. "Detection by Multiplex Polymerase Chain Reaction and Typing of *Chlamydia trachomatis* Isolates," *FEMS Microbiology Letters*, vol. 130, pp. 205-210, 1995.
International Search Report dated Apr. 13, 2004.
Supplementary European Search Report dated Jul. 4, 2006.

* cited by examiner

*Primary Examiner*—Kenneth R. Horlick
*Assistant Examiner*—David C Thomas
(74) *Attorney, Agent, or Firm*—Knobbe, Martens, Olson & Bear, LLP

(57) ABSTRACT

A method for detecting *Chlamydia trachomatis* comprising performing PCR using DNA obtained from a sample as a template and detecting an amplification product, wherein a primer pair used for PCR is designed on the basis of the nucleotide sequences of the regions corresponding to the nucleotide numbers 5157 to 5201 and 5245 to 5276 in the nucleotide sequence of SEQ ID NO: 1 so that the nucleotide sequence between the two regions can be amplified. A method for quickly detecting *Chlamydia trachomatis* with superior sensitivity and specificity is provided.

2 Claims, 1 Drawing Sheet

SEQUENCE LISTING

<160> NUMBER OF SEQ ID NOS: 7

<210> SEQ ID NO 1
<211> LENGTH: 7501
<212> TYPE: DNA
<213> ORGANISM: Chlamydia trachomatis

<400> SEQUENCE: 1

```
tttgcaactc ttggtggtag actttgcaac tcttggtggt agactttgca actcttggtg      60
gtagactttg caactcttgg tggtagactt ggtcataatg acttttgtt gaaaaatttc      120
ttaaaatctt agagctccga ttttgaatag ctttggttaa gaaatgggc tcgatggctt      180
tccataaaag taggttgttc ttaacttttg gggacgcgtc ggaaatttgg ttatctactt      240
tatctcatct aactagaaaa aattatgcgt ctgggattaa ctttcttgtt tctttagaga      300
ttctggattt atcggaaacc ttgataaagg ctatttctct tgaccacagc gaatctttgt      360
ttaaaatcaa gtctctagat gttttaatg gaaagtcgt ttcagaggcc tctaaacagg       420
ctagagcggc atgctacata tcttcacaa gttttttgta tagattgacc aagggatata      480
ttaaacccgc tattccattg aaagattttg gaaacactac attttttaaa atccgagaca      540
aaatcaaaac agaatcgatt tctaagcagg aatggacagt ttttttttgaa gcgctccgga      600
tagtgaatta tagagactat ttaatcggta aattgattgt acaagggatc cgtaagttag      660
acgaaatttt gtcttttgcgc acagacgatc tatttttttgc atccaatcag atttcctttc      720
gcattaaaaa aagacagaat aaagaaacca aaattctaat cacatttcct atcagcttaa      780
tggaggagtt gcaaaaatac acttgtggga gaaatgggag agtatttgtt tctaaaatag      840
ggattcctgt aacaacaagt caggttgcgc ataattttag gcttgcagag ttctatagtg      900
ctatgaaaat aaaaattact cctagagtac ttcgtgcaag cgctttgatt catttaaagc      960
aaataggatt aaaagatgag gaaatcatgc gtatttcctg tcttcatcg agacaaagtg     1020
tgtgttctta ttgttctggg gaagaggtaa gtcctctagt acaaacaccc ccaatattgt     1080
gatataatta aaattatatt catattctgt tgccagaaaa aacacttta ggctatatta      1140
gagccaatct tctttgaagc gttgtcttct cgagaagatt tatcgtacgc aaatatcatc     1200
tttgcggttg cgtgtcctgt gaccttcatt atgtcggagt ctgagcaccc taggcgtttg     1260
tactccgtca cagcggttgc tcgaagcacg tgcggggtta tcttaaaagg gattgcagct     1320
tgtagtcctg cttgagagaa cgtgcgggcg atttgcctta accccaccat ttttccggag     1380
cgagttacga agacaaaacc tcttcgttga ccgatgtact cttgtagaaa gtgcataaac     1440
ttctgaggat aagttataat aatcctctt tctgtctgac ggttcttaag ctgggagaaa     1500
gaaatggtag cttgttggaa acaaatctga ctaatctcca agcttaagac ttcagaggag     1560
cgtttacctc cttggagcat tgtctgggcg atcaaccaat cccgggcatt gattttttt       1620
agctctttta ggaaggacgc tgtttgcaaa ctgttcatcg catctgtttt tactatttcc     1680
ctggttttaa aaaatgttcg actattttct tgtttagaag gttgcgctat agcgactatt     1740
ccttgagtca tcctgtttag gaatcttgtt aaggaaatat agcttgctgc tcgaacttgt     1800
ttagtacctt cggtccaaga agtcttggca gaggaaactt ttttaatcgc atctagaatt     1860
agattatgat ttaaaaggga aaactcttgc agattcatat ccaaggacaa tagaccaatc     1920
ttttctaaag acaaaaaaga tcctcgatat gatctacaag tatgtttgtt gagtgatgcg     1980
gtccaatgca taataacttc gaataaggag aagcttttca tgcgtttcca ataggattct     2040
```

-continued

```
tggcgaattt ttaaaacttc ctgataagac ttttcgctat attctaacga catttcttgc      2100
tgcaaagata aatccctttt acccatgaaa tccctcgtga tataacctat ccgtaaaatg      2160
tcctgattag tgaaataatc aggttgttaa caggatagca cgctcggtat tttttttatat     2220 aaacatgaaa actcgttccg aaatagaaaa tcgcatgcaa gatatcgagt atgcgttgtt     2280
aggtaaagct ctgatatttg aagactctac tgagtatatt ctgaggcagc ttgctaatta     2340
tgagtttaag tgttctcatc ataaaaacat attcatagta tttaaatact aaaagacaa      2400 tggattacct ataactgtag actcggcttg gaagagctt ttgcggcgtc gtatcaaaga      2460
tatggacaaa tcgtatctcg ggttaatgtt gcatgatgct ttatcaaatg acaagcttag     2520
atccgtttct catacggttt tcctcgatga tttgagcgtg tgtagcgctg aagaaaattt     2580
gagtaatttc attttccgct cgtttaatga gtacaatgaa aatccattgc gtagatctcc     2640
gtttctattg cttgagcgta aaagggaag cttgacagt gctatagcaa agacttttc       2700 tattcgcagc gctagaggcc ggtctattta tgatatattc tcacagtcag aaattggagt    2760
gctggctcgt ataaaaaaaa gacgagcaac gttctctgag aatcaaaatt ctttctttga    2820
tgccttccca acaggataca aggatattga tgataaagga gttatcttag ctaaaggtaa    2880
tttcgtgatt atagcagcta ggccatctat agggaaaact gctttagcta tagacatggc    2940
gataaatctt gcggttactc aacagcgtag agttggtttc ctatctctag aaatgagcgc    3000
aggtcaaatt gttgagcgga ttattgctaa tttaacagga atatctggtg aaaaattaca    3060 aagagggat ctctctaaag aagaattatt ccgagtagaa gaagctggag aaacagttag    3120
agaatcacat ttttatatct gcagtgatag tcagtataag cttaatttaa tcgcgaatca    3180
gatccggttg ctgagaaaag aagatcgagt agacgtaata tttatcgatt acttgcagtt    3240
gatcaactca tcggttggag aaaatcgtca aaatgaaata gcagatatat ctagaaccctt   3300 aagaggttta gcctcagagc taaacattcc tatagtttgc ttatcccaac tatctagaaa    3360
agttgaggat agagcaaata aagttcccat gctttcagat ttgcgagaca gcggtcaaat    3420
agagcaagac gcagatgtga ttttgtttat caataggaag gaatcgtctt ctaattgtga    3480
gataactgtt gggaaaaata gacatggatc ggttttctct tcggtattac atttcgatcc    3540
aaaaattagt aaattctccg ctattaaaaa agtatggtaa attatagtaa ctgccacttc    3600
atcaaaagtc ctatccacct tgaaaatcag aagtttggaa gaagacctgg tcaatctatt    3660
aagatatctc ccaaattggc tcaaatggg atggtagaag ttataggtct tgattttctt     3720
tcatctcatt accatgcatt agcagctatc caaagattgc tgactgcaac gaattacaag   3780
gggaacacaa aagggggttgt tttatccaga gaatcaaata gttttcaatt tgaaggatgg    3840
ataccaagaa tccgttttac aaaaactgaa ttcttagagg cttatggagt taagcggtat    3900
aaaacatcca gaaataagta tgagtttagt ggaaaagaag ctgaaactgc tttagaagcc   3960
ttataccatt taggacatca accgttttta atagtggcaa ctagaactcg atggactaat    4020
ggaacacaaa tagtagaccg ttaccaaact ctttctccga tcattaggat ttacgaagga   4080
tgggaaggtt taactgacga agaaaatata gatatagact taacaccttt taattcacca   4140
tctacacgaa aacataaagg gttcgttgta gagccatgtc ctatcttggt agatcaaata   4200
gaatcctact ttgtaatcaa gcctgcaaat gtataccaag aaataaaaat gcgcttccca    4260
aatgcatcaa agtatgctta cacatttatc gactgggtga ttcagcagc tgcgaaaaag    4320 agacgaaaat taactaagga taattcttgg ccagaaaact tgttcttaaa cgttaacgtt    4380
```

```
aaaagtcttg catatatttt aaggatgaat cggtacattt gtacaaggaa ctggaaaaaa   4440
atcgagttag ctatcgataa atgtatagaa atcgccattc agcttggttg gttatctaga   4500
agaaaacgca ttgaatttct ggattcttct aaactctcta aaaagaaat tctatatcta    4560 aataaagagc gttttgaaga aataaccaag aaatctaaag aacaaatgga acaattagaa   4620
caagaatcta ttaattaata gcaaacttga aactaaaaac ctaatttatt taaagctcaa   4680
aataaaaaag agttttaaaa tgggaaattc tggttttat ttgtataaca ctcaaaactg    4740
cgtctttgct gataatatca aagttgggca aatgacagag ccgctcaagg accagcaaat   4800
aatccttggg acaacatcaa cacctgtcgc agccaaaatg acagcttctg atggaatatc   4860
tttaacagtc tccataatc catcaaccaa tgcttctatt acaattggtt tggatgcgga    4920
aaaagcttac cagcttattc tagaaaagtt gggagatcaa attcttggtg gaattgctga   4980
tactattgtt gatagtacag tccaagatat tttagacaaa atcacaacag acccttctct   5040
aggtttgttg aaagctttta caacttccc aatcactaat aaaattcaat gcaacgggtt    5100
attcactccc aggaacattg aaactttatt aggaggaact gaaataggaa aattcacagt   5160
cacacccaaa agctctggga gcatgttctt agtctcagca gatattattg catcaagaat   5220
ggaaggcggc gttgttctag cttttggtacg agaaggtgat tctaagccct acgcgattag  5280
ttatggatac tcatcaggcg ttcctaattt atgtagtcta agaaccagaa ttattaatac   5340
aggattgact ccgacaacgt attcattacg tgtaggcggt ttagaaagcg gtgtggtatg   5400
ggttaatgcc ctttctaatg gcaatgatat tttaggaata acaaatactt ctaatgtatc   5460 tttttttggag gtaataccct aaacaaacgc ttaaacaatt tttattggat ttttcttata  5520
ggttttatat ttagagaaaa aagttcgaat tacggggttt gttatgcaaa ataaaagcaa   5580
agtgagggac gattttatta aaattgttaa agatgtgaaa aaagatttcc ccgaattaga   5640
cctaaaaata cgagtaaaca aggaaaaagt aactttctta aattctccct tagaactcta   5700
ccataaaagt gtctcactaa ttctaggact gcttcaacaa atagaaaact ctttaggatt   5760
attcccagac tctcctgttc ttgaaaaatt agagggataac agtttaaagc taaaaaaggc   5820
tttgattatg cttatcttgt ctagaaaaga catgtttttcc aaggctgaat agataactta   5880
ctctaacgtt ggagttgatt tgcacacctt agtttttgc tcttttaagg gaggaactgg    5940
aaaaacaaca ctttctctaa acgtgggatg caacttggcc caattttag ggaaaaaagt    6000 gttacttgct gacctagacc cgcaatccaa tttatcttct ggattggggg ctagtgtcag   6060
aagtaaccaa aaaggcttac acgacatagt atacacatca aacgatttaa aatcaatcat   6120
ttgcgaaaca aaaaaagata gtgtggacct aattcctgca tcattttat ccgaacagtt    6180 tagagaattg gatattcata gaggacctag taacaactta aagttattcc tgaatgagta   6240
ctgcgctcct ttttatgaca tctgcataat agacactcca cctagcctag gagggttaac   6300
gaaagaagct tttgttgcag gagacaaatt aattgcttgt ttaactccag aacctttttc   6360
tattctaggg ttacaaaaga tacgtgaatt cttaagttcg gtcggaaaac ctgaagaaga   6420
acacattctt ggaatagctt tgtctttttg ggatgatcgt aactcgacta accaaatgta   6480
tatagacatt atcgagtcta tttacaaaaa caagcttttt tcaacaaaaa ttcgtcgaga   6540
tatttctctc agccgttctc ttcttaaaga agattctgta gctaatgtct atccaaattc   6600
tagggccgca aagatattc tgaagttaac gcatgaaata gcaaatattt tgcatatcga    6660
atatgaacga gattactctc agaggacaac gtgaacaaac taaaaaaaga agcgaatgtc   6720
ttttttaaaa aaaatcaaac tgccgcttct ttagatttta agaagacgct tccttccatt   6780
```

```
gaactattct cagcaacttt gaattctgag gaaagtcaga gtttggatca attatttta      6840 tcagagtccc aaaactattc ggatgaagaa ttttatcaag aagacatcct agcggtaaaa      6900
ctgcttactg gtcagataaa atccatacag aagcaacacg tacttctttt aggagaaaaa      6960
atctataatg ctagaaaaat cctgagtaag gatcacttct cctcaacaac ttttcatct      7020 tggatagagt tagttttag aactaagtct tctgcttaca atgctcttgc atattacgag      7080 cttttata acctccccaa ccaaactcta caaaagagt ttcaatcgat ccctataaa      7140 tccgcatata ttttggccgc tagaaaaggc gatttaaaaa ccaaggtcga tgtgataggg      7200
aaagtatgtg gaatgtcgaa ctcatcggcg ataagggtgt tggatcaatt tcttccttca      7260
tctagaaaca aagacgttag agaaacgata gataagtctg attcagagaa gaatcgccaa      7320
ttatctgatt tcttaataga gatacttcgc atcatgtgtt ccggagttc tttgtcctcc      7380 tataacgaaa atcttctaca acagttttt gaactttta agcaaaagag ctgatcctcc      7440
gtcagctcat atatatatct attatatata tatatttagg gatttgattt tacgagagag      7500
a                                                                       7501

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
cagtcacacc caaaagctct gggagcatg                                          29

<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3
agctctggga gcatgttctt agtctcagca g                                       31

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
agctctggga gcatgttctt agtctc                                             26

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
tcgcgtaggg cttagaatca ccttc                                              25

<210> SEQ ID NO 6
<211> LENGTH: 31
<212> TYPE: DNA
```

-continued

```
<213> ORGANISM: Artificial Sequence
<220> FEATURE:
<223> OTHER INFORMATION: primer

<400> SEQUENCE: 6
tcgcgtaggg cttagaatca ccttctcgta c                                31

<210> SEQ ID NO 7
<211> LENGTH: 36
<212> TYPE: DNA
<213> ORGANISM: Artificial Sequence
<220> FEATURE:
<223> OTHER INFORMATION: probe

<400> SEQUENCE: 7
caaagctaga acaacgccgc cttccattct tgatgc                           36
```

METHOD FOR DETECTING *CHLAMYDIA TRACHOMATIS* AND KIT THEREFOR

RELATED APPLICATIONS

This is the U.S. National Phase under 35 U.S.C. § 371 of International Application PCT/JP2004/002435, filed Feb. 27, 2004, which was published in a language other than English, which claims priority of JP 2003-050662, filed Feb. 27, 2003.

TECHNICAL FIELD

The present invention relates to a method for detecting *Chlamydia trachomatis* and a kit therefore.

BACKGROUND ART

*Chlamydia trachomatis* is one of nongonococcal urethritis pathogens, and as a method of detecting it, a method of amplifying a partial sequence of a cryptic plasmid existing in *Chlamydia trachomatis* cells in a multiple copy number by a gene amplification method and detecting the amplification product is known (Japanese Patent Nos. 2719225 and 3127135).

DISCLOSURE OF THE INVENTION

An object of the present invention is to provide a method for quickly detecting *Chlamydia trachomatis* with superior sensitivity and specificity and a kit therefor.

The inventors of the present invention found that, if PCR was performed with primers designed for a specific region in the cryptic plasmid pLGV440 of *Chlamydia trachomatis*, *Chlamydia trachomatis* could be quickly detected, and thus accomplished the present invention.

The present invention provides a method for detecting *Chlamydia trachomatis* comprising performing PCR using DNA obtained from a sample as a template and detecting an amplification product, wherein a primer pair used for PCR is designed on the basis of the nucleotide sequences of the regions corresponding to the nucleotide numbers 5157 to 5201 and 5245 to 5276 in the nucleotide sequence of SEQ ID NO: 1 so that the nucleotide sequence between the two regions can be amplified (detection method of the present invention).

The present invention also provides a kit used for the method of the present invention, that is, a kit for detection of *Chlamydia trachomatis* by performing PCR using DNA obtained from a sample as a template, which comprises a primer pair designed on the basis of the nucleotide sequences of the regions corresponding to the nucleotide numbers 5157 to 5201 and 5245 to 5276 in the nucleotide sequence of SEQ ID NO: 1 so that the nucleotide sequence between the two regions can be amplified (detection kit of the present invention).

In the present invention, the primer pair preferably consists of an oligonucleotide having an nucleotide sequence of SEQ ID NO: 2, 3 or 4 and an oligonucleotide having a nucleotide sequence of SEQ ID NO: 5 or 6, more preferably an oligonucleotide having the nucleotide sequence of SEQ ID NO: 3 and an oligonucleotide having the nucleotide sequence of SEQ ID NO: 5, or an oligonucleotide having the nucleotide sequence of SEQ ID NO: 4 and an oligonucleotide having the nucleotide sequence of SEQ ID NO: 6.

The present invention also provides a hybridization probe containing an oligonucleotide designed on the basis of the nucleotide sequence of the region corresponding to the nucleotide numbers 5210 to 5245 in the nucleotide sequence of SEQ ID NO: 1 and a label.

The nucleotide sequence of SEQ ID NO: 1 is the nucleotide sequence of the cryptic plasmid pLGV440 of the *Chlamydia trachomatis* (GenBank accession number X06707), and those skilled in the art can easily identify and recognize the region specified by the nucleotide numbers of the nucleotide sequence of SEQ ID NO: 1 also in a strain having a mutation in pLGV440 by taking difference in the nucleotide sequence that may exist depending on individuals or the like into consideration.

BEST MODE FOR CARRYING OUT THE INVENTION

Figure 1:
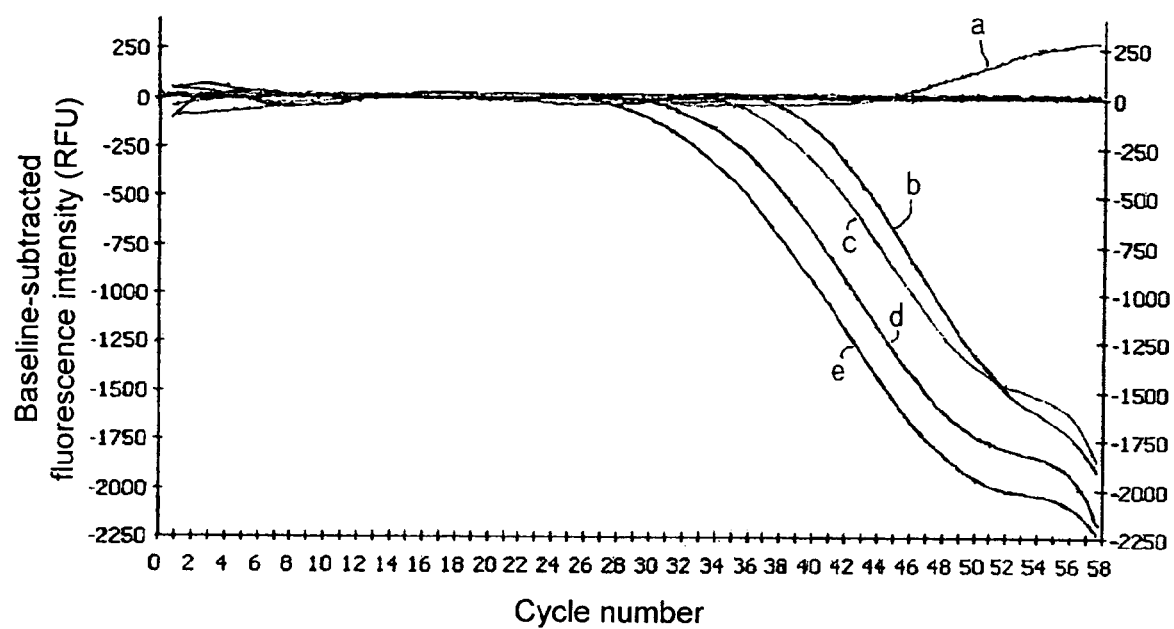
FIG. 1 shows a production time course of an amplification product (detection results of real-time PCR): a: no copy, b: 2 copies, c: 20 copies, d: 200 copies, and e: 2000 copies.

<1> Detection Method of the Present Invention

The detection method of the present invention is a method for detecting *Chlamydia trachomatis* comprising performing PCR using DNA obtained from a sample as a template and detecting an amplification product, wherein a primer pair used for PCR is designed on the basis of the nucleotide sequences of the regions corresponding to the nucleotide numbers 5157 to 5201 and 5245 to 5276 in the nucleotide sequence of SEQ ID NO: 1 so that the nucleotide sequence between the two regions can be amplified.

The sample is not particularly limited so long as it contains or possibly contains *Chlamydia trachomatis*. Examples thereof include urine, urethra swab, cervical swab and so forth. From these samples, DNA can be obtained by a usual method under conditions where DNA of the cryptic plasmid of *Chlamydia trachomatis* can be prepared.

PCR in the detection method of the present invention can be performed according to a usual PCR procedure except that DNA obtained from the sample is used as a template, and that the specific primer pair is used.

The primer pair used in the present invention is designed on the basis of a nucleotide sequence of a region corresponding to the nucleotide numbers 5157 to 5201 in the nucleotide sequence of SEQ ID NO: 1 (first region) and a nucleotide sequence of a region corresponding to the nucleotide numbers 5245 to 5276 (second region) so that the nucleotide sequence between the two regions can be amplified.

The length of the primers is usually 10 to 40 nucleotides. Further, the position in each region and the length of the primers are preferably set so that the Tm value should become 55 to 70° C., and thus the annealing temperature used in PCR can be set to be relatively high. The Tm value used herein is a value calculated by the nearest neighbor base pair analysis. The primers constituting the primer pair are preferably designed to have substantially the same Tm values.

Specific examples of the primer designed on the basis of the first region include a primer having the nucleotide sequence of SEQ ID NO: 2 (corresponding to the nucleotide numbers 5157 to 5185 in the nucleotide sequence of SEQ ID NO: 1) or a nucleotide sequence complementary thereto, a primer having the nucleotide sequence of SEQ ID NO: 3 (corresponding to the nucleotide numbers 5171 to 5201 in the nucleotide sequence of SEQ ID NO: 1) or a nucleotide sequence complementary thereto, and a primer having the nucleotide sequence of SEQ ID NO: 4 (corresponding to the nucleotide numbers 5171 to 5196 in the nucleotide sequence of SEQ ID NO: 1) or a nucleotide sequence complementary thereto. Examples of the primer designed on the basis of the second region include a primer having the nucleotide sequence of SEQ ID NO: 5 (corresponding to the nucleotide numbers 5276 to 5252 in the nucleotide sequence of SEQ ID NO: 1) or a nucleotide sequence complementary thereto, and a primer having the nucleotide sequence of SEQ ID NO: 6 (corresponding to the nucleotide numbers 5276 to 5246 in the nucleotide sequence of SEQ ID NO: 1) or a nucleotide sequence complementary thereto.

The primer pair is designed so that the nucleotide sequence between the two regions can be amplified, that is, one primer should be a sense primer and the other primer should be an antisense primer. Because the cryptic plasmid is a cyclic plasmid, it has two nucleotide sequences between the two regions. However, the primers are usually designed so that a shorter nucleotide sequence should be amplified.

Preferred examples of the primer pair include a combination of an oligonucleotide having a nucleotide sequence of SEQ ID NO: 2, 3 or 4 and an oligonucleotide having a nucleotide sequence of SEQ ID NO: 5 or 6. Further, more preferred examples of the primer pair include a combination of an oligonucleotide having the nucleotide sequence of SEQ ID NO: 3 and an oligonucleotide having the nucleotide sequence of SEQ ID NO: 5 and a combination of an oligonucleotide having the nucleotide sequence of SEQ ID NO: 4 and an oligonucleotide having the nucleotide sequence of SEQ ID NO: 6.

The primer pair for the aforementioned specific regions can be designed by a method known to those skilled in the art taking PCR conditions into consideration. The primer pair can be designed by using a computer program for designing primers.

The primers may be designed as a mixed primer obtained by mixing two or more kinds of primers for one or both of the sense primer and the antisense primer. When a mutation of a nucleotide exists in the region for which the primer is designed, detection efficiency can be improved by using a mixed primer.

Although the PCR conditions may be determined according to a usual PCR method, the annealing temperature should be set to be relatively high due to the use of the aforementioned specific primer pair. The annealing temperature is usually 50 to 70° C. Because the annealing temperature is relatively high, the conditions for two-step PCR in which annealing and elongation are performed under the same conditions may be determined.

A typical example of composition of the PCR reaction mixture is as follows.

| | |
|---|---|
| DNA fragments | 1 molecule or more |
| Primers | 100 to 2000 nM |
| Nucleotides | 100 to 500 µM for each |
| DNA polymerase | 0.25 to 1.25 Units/µl |
| Tris-HCl (pH 7 to 9) | 1 to 5 mM |
| MgCl$_2$ | 1.5 to 5 mM |
| Surfactant or gelatin | 0 to 25% |
| (Final volume: 25 to 100 µl) | |

Further, a typical example of the temperature cycle is as follows, and such a temperature cycle is usually repeated 30 to 60 times.
(1) Denaturation: 90 to 95° C., 1 to 60 seconds
(2) Annealing: 55 to 70° C., 6 to 60 seconds
(3) Elongation: 72 to 75° C., 6 to 60 seconds A typical example of the temperature cycle for the two-step PCR is as follows, and this temperature cycle is usually repeated 30 to 60 times.
(1) Denaturation: 90 to 95° C., 1 to 60 seconds
(2) Annealing and elongation: 55 to 70° C., 6 to 60 seconds In the detection method of the present invention, the amplification product can be detected by a usual method for detecting amplification products. For example, the amplification product may be detected by agarose gel electrophoresis, or by real time PCR, in which PCR is performed in the presence of a substance of which fluorescence changes when it binds to the amplification product (for example, a fluorescent dye of which fluorescence intensity changes when it binds to a double-stranded DNA, a hybridization probe designed so that it should hybridize with a single-stranded DNA, and fluorescence intensity thereof should change due to fluorescence resonance energy transfer (FRET) upon hybridization, and so forth), and then fluorescence is measured.

According to the detection method of the present invention, primers having a relatively high Tm value can be designed for specified regions, and therefore the annealing temperature used in PCR can be made relatively high. Accordingly, the time required to lower temperature from the denaturation temperature to the annealing temperature is reduced. Further, non-specific amplification is reduced due to the high annealing temperature. Furthermore, two-step PCR in which annealing and elongation are performed under the same conditions is also possible. As a result, quicker gene amplification is enabled.

The present invention also provides a hybridization probe suitable for detection by hybridization. Examples of such a hybridization probe include a probe comprising an oligonucleotide designed on the basis of a nucleotide sequence of a region corresponding to the nucleotide numbers 5210 to 5245 in the nucleotide sequence of SEQ ID NO: 1 and a label. This oligonucleotide may be complementary to a sense chain or complementary to an antisense chain.

The chain length and Tm value of the oligonucleotide of the hybridization probe are suitably determined depending on the hybridization conditions. The length of this oligonucleotide is usually 25 to 45 nucleotides, and the Tm value is usually 50 to 70° C. When the hybridization probe is used for real-time PCR, the Tm value of the oligonucleotide is preferably set to be higher than the Tm value of the primer by 2 to 5° C. so that the probe should hybridize with a target sequence before hybridization of the primer. Examples of such an oligonucleotide include an oligonucleotide having the nucleotide sequence of SEQ ID NO: 7.

The hybridization probe can be labeled in such a manner that the hybridization should not be inhibited under the hybridization conditions. The hybridization probe for real-time PCR is preferably labeled in such a manner that fluorescence intensity should change when it hybridizes with a single-stranded DNA.

In the detection method of the present invention, the amplification product is preferably detected by a detection method using the hybridization probe of the present invention.

<2> Detection Kit of the Present Invention

The detection kit of the present invention is a kit usable for the detection method of the present invention, that is, a kit for detection of *Chlamydia trachomatis* by performing PCR using DNA obtained from a sample as a template, which is characterized by including a primer pair designed on the basis of the nucleotide sequences of the regions corresponding to the nucleotide numbers 5157 to 5201 and 5245 to 5276 in the nucleotide sequence of SEQ ID NO: 1 so that the nucleotide sequence between the two regions can be amplified.

The primer pair is as described above with regard to the detection method of the present invention.

In the kit of the present invention, the primers of the primer pair may be included as a mixture or included separately.

The kit of the present invention may further include reagents required for PCR and/or detection of an amplification product in addition to the primer pair. Examples of such reagents include the aforementioned hybridization probe.

EXAMPLES

Hereafter, the present invention will be explained more specifically with reference to the following examples.

Example 1

Detection by PCR

From the first region (nucleotide numbers 5157 to 5201) and the second region (nucleotide number 5245 to 5276) of the nucleotide sequence of the cryptic plasmid of *Chlamydia trachomatis* (SEQ ID NO: 1, GenBank accession number X06707), nucleotide sequences having a high GC content (48 to 55%) and high Tm value (63 to 65° C. (calculated by the nearest neighbor base pair method)) were selected. That is, 3 types of upstream primers (SEQ ID NOS: 2, 3 and 4) and 2 types of downstream primers (SEQ ID NOS: 5 and 6) were selected as target binding sequences. Then, oligonucleotides having these target binding sequences were synthesized as primers.

TABLE 1

Upstream (forward) primers:
CT-F5157-29:
                                            (SEQ ID NO:2)
cag tca cac cca aaa gct ctg gga gca tg CT-F5171-31:
                                            (SEQ ID NO:3)
agc tct ggg agc atg ttc tta gtc tca gca g CT-F5171-26:
                                            (SEQ ID NO:4)
agc tct ggg agc atg ttc tta gtc tc Downstream (reverse) primers:
CT-R5276-25:
                                            (SEQ ID NO:5)
tcg cgt agg gct tag aat cac ctt c CT-R5276-31:
                                            (SEQ ID NO:6)
tcg cgt agg gct tag aat cac ctt ctc gta c Three kinds of pairs each consisting of a combination of the aforementioned upstream and downstream amplification primers (SEQ ID NOS: 2-5, 3-5 and 4-6) were used for PCR. The reaction mixture (25 μL) contained 1×Gene Taq buffer, 0.625 U of Gene Taq polymerase (Nippon Gene), 0.2 mM each of dGTP, dCTP, dATP and dUTP, 0.5 μM each of the upstream and downstream primers, and 2 to 2000 copies of *Chlamydia trachomatis* cell genomic DNA (ATCC strain CT-VR878). To examine appropriate reaction temperature, PCR was performed by using a temperature gradient for the annealing temperature for the amplification reaction in iCycler (BIO-RAD). The reaction temperatures were as follows: 95° C. for 4 minutes, (95° C. for 30 seconds, gradient of 62 to 72° C. for 30 seconds, 72° C. for 30 seconds)×50 cycles, and 72° C. for 7 minutes. Occurrence of amplification was confirmed by applying the product to 3% agarose gel electrophoresis.

Whichever primer pair was used, 2 copies of *Chlamydia trachomatis* cell genomic DNA could be detected with a relatively high annealing temperature condition of 64.0 to 68.2° C.

The above results showed that the aforementioned primer sequences had superior sensitivity and specificity and were effective for reducing the reaction time.

Example 2

Detection Using Two-step PCR

Among the primer pairs used in Example 1, the primer pairs of SEQ ID NOS: 3-5 and 4-6 were used for two-step PCR. The reaction mixture (25 μL) contained 1×ΔTth buffer, 0.625 U of ΔTth (TOYOBO), 0.2 mM each of dGTP, dCTP, dATP and dUTP, 0.5 μM each of the upstream and downstream primers, and 2 to 2000 copies of *Chlamydia trachomatis* cell genomic DNA (ATCC strain CT-VR878). The reaction temperatures were as follows: 95° C. for 1 minute, (95° C. for 15 seconds, 65 or 68° C. for 20 seconds)×2 cycles, and (90° C. for 15 seconds, 65 or 68° C. for 20 seconds)×58 cycles. The reaction was performed by using a thermal cycler (TaKaRa). Occurrence of amplification was confirmed by applying the product to 3% agarose gel electrophoresis.

When the primer pair of SEQ ID NOS: 3-5 was used, 2 copies of *Chlamydia trachomatis* cell genomic DNA could be detected with an annealing temperature of 68° C. When the primer pair of SEQ ID NOS: 4-6 was used, 2 copies of *Chlamydia trachomatis* cell genomic DNA could be detected with an annealing temperature of 65° C.

The above results showed that it was possible to perform two-step PCR in which the reaction time could be further reduced.

Example 3

Detection Using Real-time PCR

Among the primer pairs used in Example 1, the primer pair of SEQ ID NOS: 3-5 was used for two-step PCR. The reaction mixture (25 μL) contained 1×ΔTth buffer, 0.625 U of ΔTth (TOYOBO), 0.2 mM each of dGTP, dCTP, dATP and dUTP, 1 μM of the upstream primer, 0.5 μM of the downstream primer, 0.2 μM of a probe for real-time detection (5FL-CT-5210-36: 5'-caa agc tag aac aac gcc gcc ttc cat tct tga tgc-3' (SEQ ID NO: 7), c at the 5' end was labeled with a fluorescent dye, type of the marker: BODIPY-FL (Molecular Probe)), and 2 to 2000 copies of *Chlamydia trachomatis* cell genomic DNA (ATCC strain CT-VR878). The reaction temperatures were as follows: 95° C. for 1 minute, (95° C. for 15 seconds, 65° C. for 20 seconds)×2 cycles, (90° C. for 15 seconds, 65° C. for 20 seconds)×58 cycles. The reaction was performed in iCycler (BIO-RAD). The real-time detection procedure was according to Japanese Patent Laid-open Publication (Kokai) No. 2001-286300.

The results are shown in FIG. 1. With the primer pair used in this example, 2 copies of *Chlamydia trachomatis* cell genomic DNA could be detected in real time with an annealing temperature of 65° C.

INDUSTRIAL APPLICABILITY

The present invention provides a method for quickly detecting *Chlamydia trachomatis* with superior sensitivity and specificity.

What is claimed is:

1. A method for detecting *Chlamydia trachomatis* comprising performing PCR using DNA obtained from a sample as a template and detecting an amplification product, wherein a primer pair used for PCR consists of an oligonucleotide having the nucleotide sequence of SEQ ID NO: 2, 3 or 4 and an oligonucleotide having the nucleotide sequence of SEQ ID NO: 5 or 6, and wherein performing PCR comprises annealing at a temperature of 64 to 68.2° C.

2. The method according to claim 1, wherein the primer pair consists of an oligonucleotide having the nucleotide sequence of SEQ ID NO: 3 and an oligonucleotide having the nucleotide sequence of SEQ ID NO: 5, or an oligonucleotide having the nucleotide sequence of SEQ ID NO: 4 and an oligonucleotide having the nucleotide sequence of SEQ ID NO: 6.

* * * * *